United States Patent [19]

Sohngen

[11] Patent Number: 4,881,535

[45] Date of Patent: Nov. 21, 1989

[54] INTRAMEDULLARY ROD TARGETING DEVICE

[76] Inventor: Gary W. Sohngen, 2101 Paseo Del Mar, San Pedro, Calif. 90732

[21] Appl. No.: 240,937

[22] Filed: Sep. 6, 1988

[51] Int. Cl.$^4$ ............................................. A61B 17/56
[52] U.S. Cl. ........................................ 606/98; 606/64
[58] Field of Search ........... 128/92 Y, 92 YZ, 92.YY, 128/92 YK, 92 VD, 92 VL, 92 V

[56] References Cited

U.S. PATENT DOCUMENTS

| | | | |
|---|---|---|---|
| 3,814,089 | 6/1974 | Deyerle | 128/92 VD |
| 4,103,683 | 8/1978 | Neufeld | 128/92 VD X |
| 4,281,649 | 8/1981 | Derweduwen | 128/92 YZ X |
| 4,541,424 | 9/1985 | Grosse et al. | 128/92 YY X |
| 4,622,959 | 11/1986 | Marcus | 128/92 YZ |
| 4,667,664 | 5/1987 | Taylor et al. | 128/92 YY X |
| 4,705,027 | 11/1987 | Klaue | 128/92 VD X |

FOREIGN PATENT DOCUMENTS

| | | | |
|---|---|---|---|
| 825047 | 5/1981 | U.S.S.R. | 128/92 VD |
| 992045 | 2/1983 | U.S.S.R. | 128/92 YY |

OTHER PUBLICATIONS

The Lancet, Jul. 17, 1937, pp. 126–128, by K. H. Pridie.

Primary Examiner—Robert A. Hafer
Assistant Examiner—Kevin G. Rooney
Attorney, Agent, or Firm—Grant L. Hubbard

[57] ABSTRACT

An intramedullary rod targeting device for guiding drilling of distal fastener screw passages in the femur of a patient during the installation in the patient's femur of an intramedullary rod is disclosed.

7 Claims, 2 Drawing Sheets

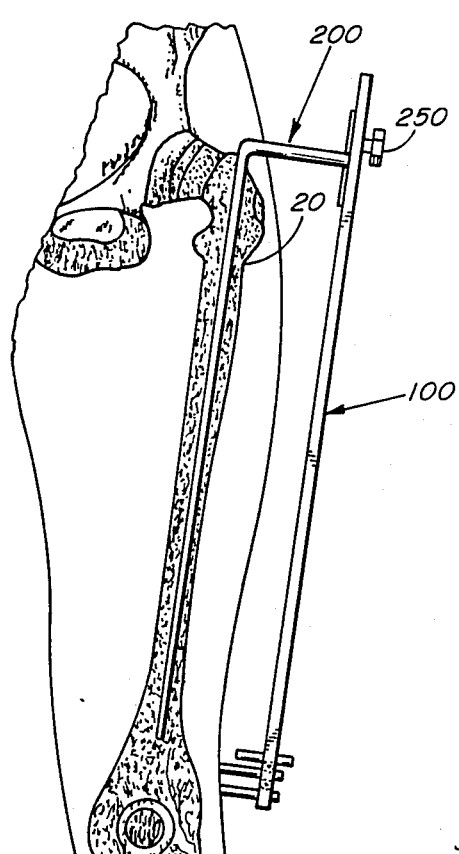
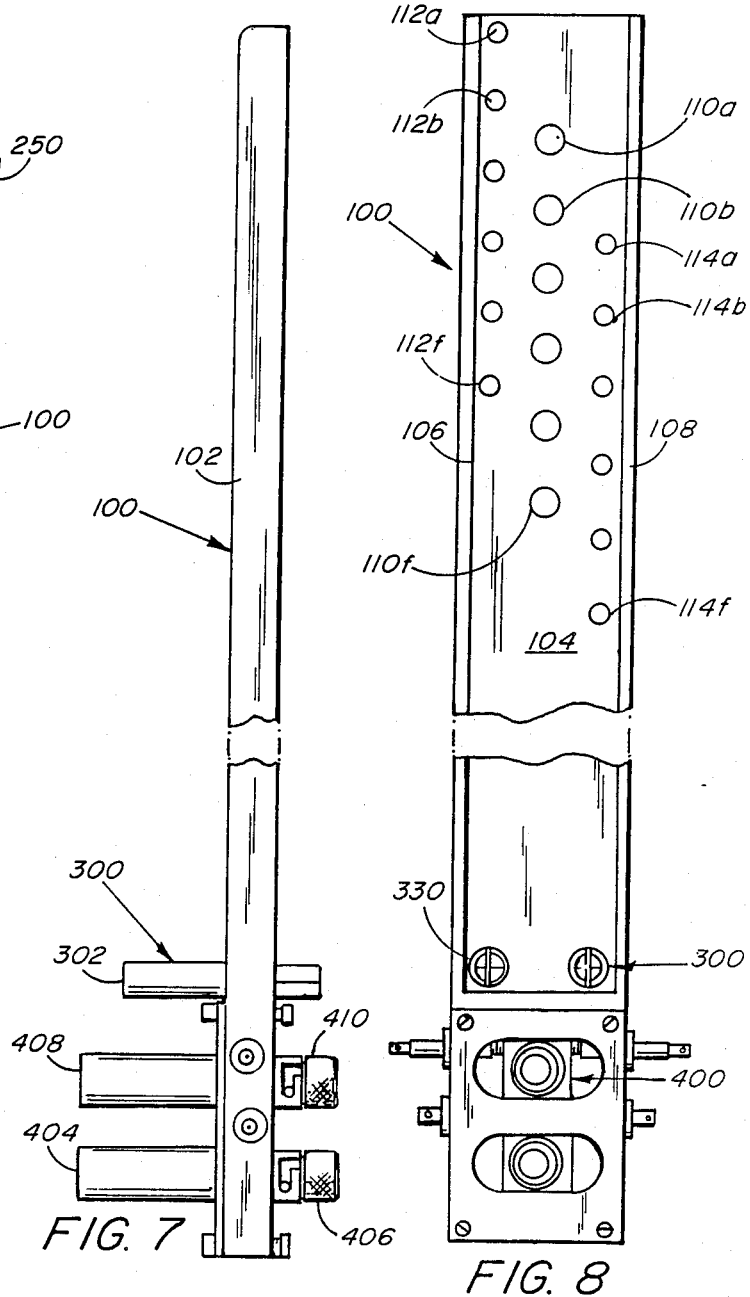
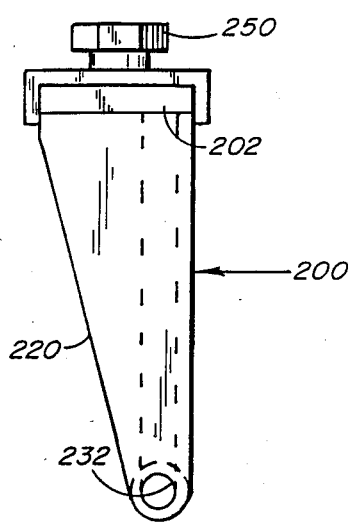
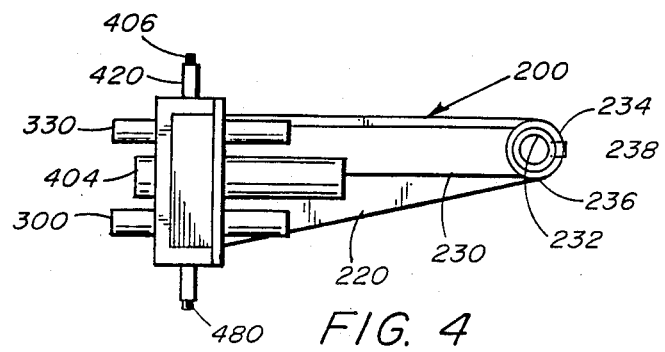

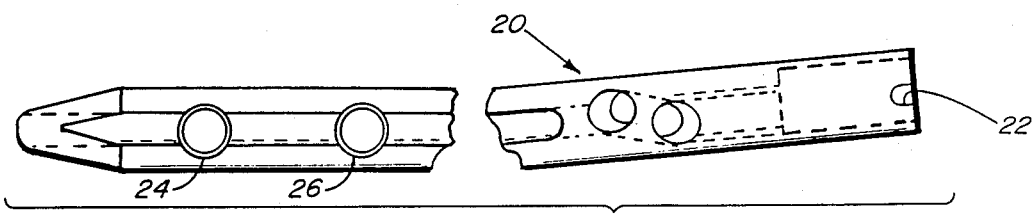
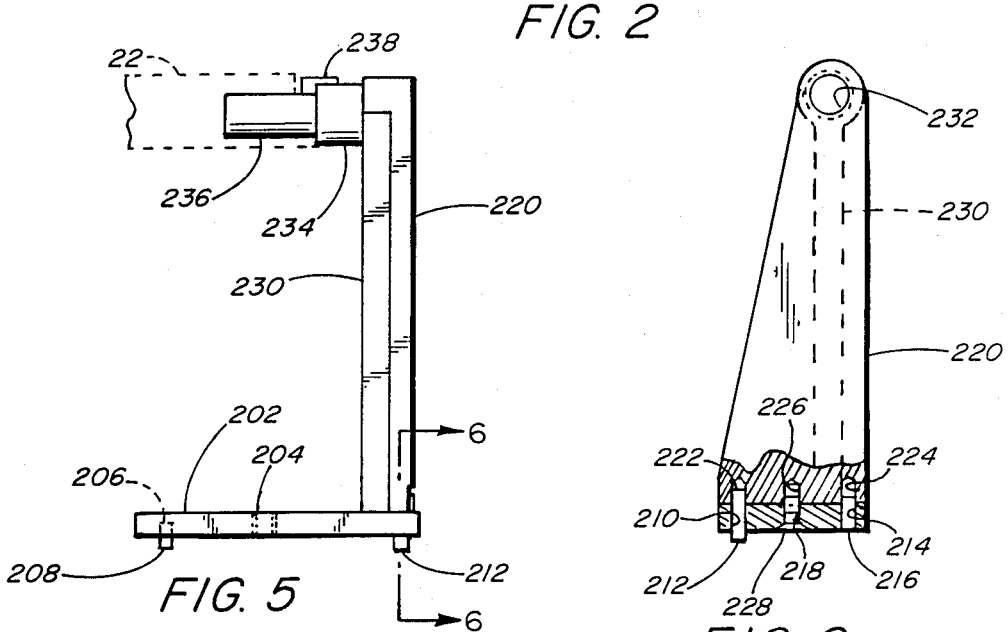
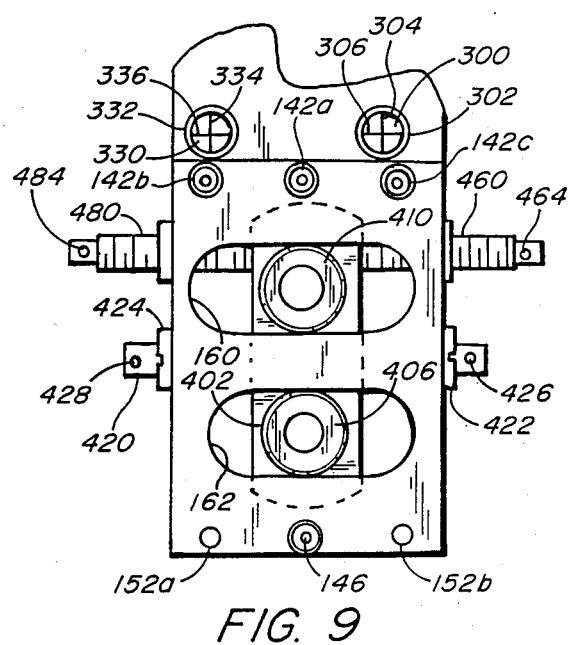
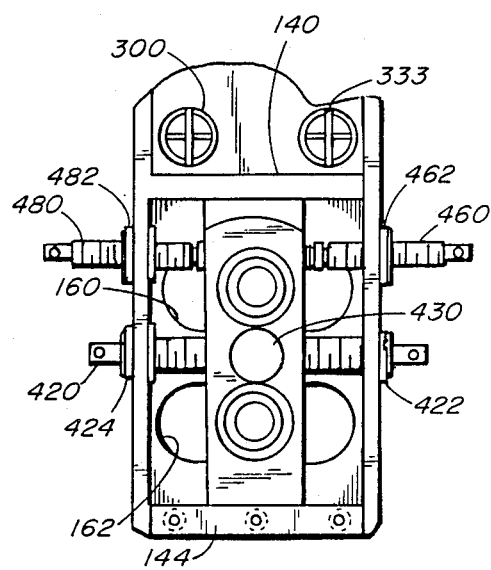

INTRAMEDULLARY ROD TARGETING DEVICE

FIELD OF THE INVENTION

This invention relates to surgical devices and, more particularly, to devices for positioning intramedullary rods in the femur of a patient and for targeting the screws for passage through apertures in the intramedullary rod for affixing the rod in the femur.

BACKGROUND OF THE INVENTION

Intramedullary rods are widely used in orthopedic surgery to fix certain broken bones and to maintain the bone fragments in the proper alignment during healing and to provide strength during the convalescence of the patient.

One such intramedullary rod with which the present invention is most useful is described by Zindrick and the present inventor in copending patent application Serial No. 230,563, filed Aug. 10, 1988. This intramedullary rod is described generally herein, but reference is made to said patient application for a more complete and detailed description.

It is necessary, in most instances, to affix the intramedullary rod to one or both fragments of the bone using bone screws or other fasteners. Thus, intramedullary rods are provide with a plurality of apertures therethrough for receiving screws or fasteners of various configurations. Fixation of the intramedullary rod requires that these apertures be precisely located, that passages be drilled through the compact cortical tissue and the cancellous tissue of the bone and that the fastener screws be secured in the bone tissue through the apertures in the intramedullary rod to fix the intramedullary rod in the proper relationship with the bone fragments.

X-ray viewers or x-ray films are widely used to display the relationship of the bone fragments, intramedullary rod and, after installation, the fastener screws. Many such viewing devices and systems are available.

The Zindrick intramedullary rod provides improved results in permitting proper healing of the femur and ease of use. The present invention comprises targeting device specifically designed to guide the installation of distal bone screws through apertures in the Zindrick intramedullary rod, but may be used with any intramedullary rod which includes distal fixation apertures in suitable locations.

SUMMARY OF THE INVENTION

This invention comprises apparatus and methods for locating the apertures and the alignment thereof during installation of intramedullary rods, and, in particular, during the installation of intramedullary rods of the type which will be identified herein for convenience as the Zindrick intramedullary rod.

The invention is described as an intramedullary rod targeting device for guiding drilling of distal fastener screw passages in the femur of a patient during the installation in the patient's femur of an intramedulary rod. The device comprises a rigid elongate external support member adapted to reside outside the patient generally parallel to and along the patient's femur during installation of an intramedullary rod in the patient's femur. A jig removeably mount the proximal end of intramedullary rod to and spaced from the proximal end of the external support member. The jig positions the intramedullary rod generally parallel to the external support member with the axis of the fastener screw apertures in a predetermined relationship with respect to the external support member. A trochar alignment device is moveably mounted proximate the distal end of the external support member for being aligned with the axis of the fastener screw apertures through the intramedullary rod. The position and orientation of the trochar alignment device can be adjusted for guiding drills in the drilling of said fastener screw passages in the femur in alignment with the apertures through the distal end of the intramedullary rod. In the preferred embodiment, x-ray alignment guides are mounted on the external support member for positioning the external support member in a predetermined relationship with an x-ray source and viewer.

BRIEF DESCRIPTION OF THE DRAWINGS

FIG. 1 depicts the relationship of the device of this invention to the intramedullary rod in the femur of a patient during installation, the leg, femur and intramedullary rod being shown schematically in increasing density to show the relationship thereof, the exemplary installation being depicted as being performed on the left femur of a female patient.

FIG. 2 depicts the pertinent structure of the Zindrick intramedullary rod, the center portion being omitted to permit an enlarged and more detailed depiction of the end structures which are pertinent to this invention.

FIG. 3 depicts the apparatus of this invention taken from the proximal end, which, in use, would be adjacent the proximal or upper end of the femur.

FIG. 4 depicts the apparatus of this invention taken from the distal end thereof.

FIG. 5 is a side view of the interface jig which is attached, during use, as part of the present invention proximate the proximal end thereof and carries the intramedullary rod to be installed in the patient's femur.

FIG. 6 is a view from the distal side of the interface jig which is attached, during use, as part of the present invention proximate the proximal end thereof and carries the intramedullary rod to be installed in the patient's femur, a portion of which is shown in cross section taken generally along lines 6—6 of FIG. 5.

FIG. 7 is a side view of the external support assembly of the distal intramedullary rod targeting device of this invention.

FIG. 8 is a proximal face view of the external support assembly of the distal intramedullary rod targeting device of this invention.

FIG. 9 is an enlarged distal face view of the distal portion of the external support assembly of the distal intramedullary rod targeting device of this invention.

FIG. 10 is an enlarged proximal face view of the distal portion of the external support assembly of the distal intramedullary rod targeting device of this invention, comparable to the view of FIG. 9, but with the cover plate removed to show the internal structure.

FIGS. 11A and 11B depict, respectively, an incorrect and a correct x-ray view through the alignment apertures of the present invention, FIG. 11A showing the device out of alignment and FIG. 11B showing the device in alignment.

DESCRIPTION OF THE PREFERRED EMBODIMENT

The present invention comprises two major assemblies, the external support assembly 100 and the distal interface jig 200, and as part of the external support assembly 100, viewer alignment subassemblies 300 and 330, and a trochar guide assembly 400.

The external support assembly 100 comprises an elongate external channel support member 102 formed of a rigid metal, preferably titanium because of its strength-to-weight ratio and low x-ray penetration density compared with stainless steel, comprising a web portion 104 with edge flange portions 106 and 108, the web portion being, typically, 2-5 times the width as the thickness of the flanges. The external support assembly and jig may be made of aluminum, steel or other metals, or even rigid polymers, though each of these materials suffers from some disadvantages compared with titatium. The web portion 104 has formed in it a series of connector screw apertures 110 generally along the center of the web and two series of alignment pin apertures 112 and 114, each series being in alignment along the respective sides of the web. These apertures permit the interface jig to be selectively secured at any of a number of positions proximate the proximal end of the external support assembly to accommodate different lengths of intramedullary rods, e.g. intramedullary rods from about 36 to about 46 mm in length.

The external support assembly comprises additional structure at the distal end which will be described hereinafter.

The interface jig is shown in FIGS. 3, 4, 5 and 6 is secured to the proximal end of the intramedullary rod 20, the essential structure of which is shown in FIG. 2, and to the external support assembly 100 to fix the intramedullary rod 20 as to spacing and orientation with respect to the external support assembly.

The interface jig 200 comprises a base plate 202 having formed generally centrally therein a threaded aperture 204, a blind aperture 206 which receives a guide pin 208 which protrudes from the distal side thereof, an aperture 210 which receives a combination guide and spacer plate fixing pin 212, and an aperture 214 which receives a spacer plate fixing pin 216. The jig 200 also comprises a spacer plate 220 which is generally planar with a reinforcing rib 230, having formed in the distal end thereof a blind aperture 222 which receives in interference fit a fixing pin 212, the distal end of which also serves as a guide pin, and a blind aperture 224 which receives in interference fit the pin 216. A threaded aperture 226 is also provided generally centrally for receiving a screw 228 which secures the spacer plate to the base plate 202 at right angles thereto at the distal end thereof.

A passage 232 extends through the spacer plate proximate the proximal end thereof. A cylindrical abutment sleeves 234 and a cylindrical guide sleeve 236 are welded to, formed integrally with, or otherwise formed proximate the proximal end of the spacer plate, the passage 232 extending through the spacer plate 232, the abutment sleeve 234 and the guide sleeve 236 as a uniform cylindrical passage. A guide key 238 is formed on or attached to the jig extending radially from the cylindrical guide sleeve 236.

The guide sleeve 236 with the extending key 238 are so formed and configured and dimensioned as to receive with a snug fit the proximal end of the intramedullary rod 20, the key slot 22 receiving the key 238. The key 238 is so positioned on the guide sleeve that when the key slot 22 receives the same, the intramedullary rod 20 is positioned and oriented such that the axes of the distal screw passages, which are right cylinders with the axes thereof substantially perpendicular to the plane of the axis of the intramedullary rod in the portion through which the such passages extend. As more fully explained in the aforesaid co-pending patent application S.N. 230,563, the intramedullary rod 20 is curved in one dimension, as shown in FIG. 2, but lies in a single plane in the other dimension, which planar dimension corresponds with or is coplanar with the plane of the drawing. The passages 24 and 26 would, therefore, be substantially perpendicular to the plane of the drawing of FIG. 2. When the intramedullary rod is thus secured on the sleeve 236, the axes of the passages 24 and 26 lie, in one plane, in a single plane which is perpendicular to the plane of the web of the external support assembly, when the jig is secured thereto by any convenient means, such as a hand screw 250, as shown in FIG. 1. Thus, it is only necessary to locate the holes along the length of the external support assembly and determine the angle of the holes relative to the axis of the external support assembly.

Returning to the description of the external support assembly 100 and the subassemblies 300, 330 and 400, it will now be apparent that the purpose of this structure at the distal end of the external support assembly is to locate the passages 24 and 24 of intramedullary rod 20 after the rod is in place in the femur of the patient.

Proximal block 140, secured by a screws 142a, 142b and 142c, and distal block 144, secured by screw 146, along with the flanges of the external channel support member define the housing for the mechanism for guiding the trochars and drills for drilling the bone. It is necessary, however, to assure that the x-ray view is accurate. This requires that the X-radiation flux path be perpendicular to the plane of the external channel support assembly. This alignment is accomplished by adjusting the source of radiation and the viewer, e.g. the x-ray tube and a film holder or scintillation viewer, with respect to the targeting device of this invention such that the X-radiation is aligned with alignment guides 300 and 330. These alignment guides comprise, respectively, cylindrical guides 302 and 332 secured through apertures through the web of the external channel support member perpendicular to the web and plates 302 and 304 in guide 302 and plates 334 and 336 in guide 332. One member of each of these pairs of plates is secured perpendicular with respect to the other such member, one member being secured proximate the proximal end of the cylindrical guide, the other at the other end of such guide. These plates, in a generally columnar x-ray beam, serve, in effect, as cross-hairs. When the x-ray viewer, whether film or instrument, shows the guide cylinders as perfect circles and the plates as the same thickness crossing in the middle of the respective circles, as shown in FIG. 11B, then the x-ray source and viewer are properly aligned with the targeting device of this invention. FIG. 11A depicts one of several views which would indicate that the x-ray source and viewer were not in alignment.

In practice, only one x-ray alignment guide is normally used, and only one is needed; however, the intramedullary rod will frequently obscure a portion of one of the alignment guides, depending on the length of the intramedullary rod. Two guides are thus provided to assure the availability of at least one x-ray guide in all circumstances.

The proper angular relationship of the trochars, drills and screws is achieved by means of the trochar guide assembly 400 which is located in the housing defined by the blocks 140 and 144, the web 104 and flanges 106 and 108 of the external channel support member 102, and by a cover plate 150 which is secured by a plurality of screws 152a, 152b, 152c and 152d to the blocks. Openings 160 and 162 are milled, or otherwise formed, through the web 104 of the external channel support member 104, with aligned corresponding openings being milled, or other wise formed, through the plate 150.

Movably positioned in the housing thus defined is a trochar alignment block 402 which carries two trochar alignment cylinders 404, to which a trochar guide 406 may be removably secured by a bayonet or other securing device, and 408 to which trochar guide 410 may be secured in like manner. The trochar alignment block may be moved from side to side, laterally across the width of the external channel support member web, by screw drive 420 suitably journaled in the flanges of the external channel support member as shown at 422 and 424 with drive pins 426 and 428 extending through the respective ends to permit the screw drive to be turned in either direction. The screw drive is threadably received in a cylinder 430 which is journaled in the trochar guide block, permitting the guide block to pivot or rotate about the same. Thus, the trochar alignment block is mounted for both lateral and pivotal movement in the housing.

The pivotal movement of the trochar alignment block is controlled and the angle thereof fixed by a pair of angle adjustment screws 460 and 480 threadably received through journals 462 and 482 through the flanges of the external channel support member, having suitable pins 464 and 484, or other mechanisms to permit the ends of the screws to be gripped, on the respective ends.

Before describing the manner of operation, it is important to note that an exemplary embodiment has been described but that the precise mechanisms, connections, etc., may be varied without departing from the invention. For example, the drive screw need extend only from one side, since either side can be used to turn it. Square, hexagonal or other shaped ends may be used on the ends of the drive screw and the angle adjustment screws, the angle adjustment screws may be received through threaded apertures in the flanges, the external support member may be an I-beam member with plates on one or both sides to define the housing, weldments or other fasteners, rather than screws may be used, etc., etc., etc.

The method of using the intramedullary rod targeting device of this invention will now be described generally as it would be used in surgery; however, many of the conventional surgical techniques will not be described as they are not essential to the understanding of the invention and would inherently be used by the surgeon. Further, only that portion of the surgical procedure which is applicable to the use of the present invention will be described.

The patient is placed on a suitable fracture table to permit access to the proximal and distal areas of the femur. An incision is made in line with the fibers of the gluteus maximus and a passage is formed with an awl at the level of the fossa immediately adjacent the greater trochanter of the femur, the position of the femur, the passages in the femur, the location and orientation of the intramedullary rod and targeting device being verified at each stage of the operation using conventional x-ray viewing as previously discussed. Once the passage for the intramedullary rod is formed in the femur, the length of rod needed is ascertained by insertion of a calibrated ball-nose guide pin.

The proximal end of an intramedullary rod of the proper length is fitted over the guide sleeve 236, with the key 238 received in the key slot 22 of the rod, and the jig is secured in a location on the external support member corresponding to the rod length by means of a hand screw 250, or any convenient fastener. The sets of fastening apertures 110 and guide apertures 112 and 114 correspond to different specific intramedullary rod lengths, e.g. one set corresponds to a 36 cm intramedullary rod, another to a 38 cm intramedullary rod, etc., such that when the jig is secured in the proper set of guide apertures, the trochar guide cylinders correspond in distance from the proximal end of the intramedullary rod with the fastening apertures 24 and 26 therethrough. Thus, one variable in aligning the trochars and drills is eliminated.

Still before inserting the intramedullary rod into the passage in the femur, the drive screw and angle adjustment screws are manipulated to align the trochar guide columns and guides exactly with the fastening apertures 24 and 26. Once alignment is made and the position of the trochar alignment block is fixed, the jig is removed from the external support member and the intramedullary rod is inserted into the passage in the femur without removing it from the jig using conventional techniques, e.g. gently impacting the proximal end of the intramedullary rod to pass it into the passage in the femur.

Once the intramedullary rod is in place in the femur, the jig is reattached to the external support member in exactly the same location to which it was attached during pre-alignment, using the guide pins to assure such attachment. If the intramedullary rod were in exactly the same configuration as it was in the pre-alignment, no further alignment would be necessary; however, some straightening or bending of the intramedullary rod may occur during insertion. Thus, it is necessary to make such fine adjustments as are necessary to bring the trochar guides in to exact alignment with the fastening apertures in the intramedullary rod. This is done by positioning the x-ray source and viewer in alignment with the x-ray alignment guides, as has been previously described in some detail, to assure that the axes of the fastening apertures is aligned with or lies in a plane parallel to the axes of the trochar alignment tubes which are mounted in the external support member, and adjusting the drive screw and/or angle adjustment screws until the viewer shows the axes of fastening apertures in alignment with the trochar guide cylinders. Lateral adjustment, i.e. movement of the trochar alignment block generally transversly to the intramedullary rod, is accomplished by turning the drive screw and angular orientation, relative to the length of the intramedullary rod, is accomplished by turning the angle adustment screws. When proper alignment is accomplished the angle adjustment screws are tightened against opposite sides of the trochar alignment block to fix the angle of the trochar alignment block relative to the axis of the external support member, with the trochar alignment tubes in alignment with the axes of the fastener screw apertures in the intramedullary rod.

The trochar guides are installed in the trochar guide tubes, a suitable incision is made in alignment with the trochar guide tubes, the trochars and drills are inserted against the bone and the bone is drilled, all as in conventional surgical procedures. The fastener screws may then be inserted in the conventional manner.

The remainder of the surgical procedures and techniques are widely used and well-known and an extended discussion is inappropriate in this specification.

In summary, the present invention comprises an intramedullary rod targeting device for guiding drilling of distal fastener screw passages in the femur of a patient during the installation in the patient's femur of an intramedullary rod which comprises one or more fastener screw receiving apertures therethrough proximate the distal end thereof. The device comprises a rigid external support member adapted to reside outside the patient generally parallel to and along the patient's femur during installation of an intramedullary rod in the patient's femur, the external support member comprising an elongate channel support member comprising a web portion and edge flange portions, the web portion having formed therein connector screw apertures and alignment pin apertures. Means are provided for removably mounting the proximal end of said intramedullary rod to and spaced from the proximal end of the external support member positioning the intramedullary rod generally parallel to the external support member with the axes of the fastener screw apertures in a predetermined relationship with respect to the external support member, said means for mounting the proximal end of the intramedullary rod including an alignment pin for being received in an alignment pin aperture in the rigid support member for accommodating different lengths of intramedullary rods. Trochar alignment means movably mounted proximate the distal end of the external support member are provided for being aligned with the axes of the fastener screw apertures through the intramedullary rod, and means are provided for adjusting the position and orientation of the trochar alignment means for guiding drills in the drilling of said fastener screw passages in the femur in alignment with the apertures through the distal end of the intramedullary rod.

In certain embodiments, the trochar alignment means comprising a an elongate trochar alignment block having first and second ends, a first trochar alignment tube passing through a first passage formed in the trochar alignment block proximate one end thereof and a second trochar alignment tube passing through a second passage formed in the trochar alignment block proximate the other end thereof, and means for adjusting the position and orientation of the trochar alignment means comprising a pivot on the trochar alignment block, a lateral screw drive threadably engaged with said pivot for moving the trochar alignment block laterally with respect to the intramedullary rod and screws mounted on the rigid elongate external support member for adjusting the angle of the trochar alignment block for aligning the trochar alignment tubes with the axes of the fastener passages in the intramedullary rod for adjusting the position and orientation of the trochar alignment means for guiding drills in the drilling of said fastener screw passages in the femur in alignment with the apertures through the distal end of the intramedullary rod.

The targeting device preferably further comprises x-ray alignment means mounted on the external support member for positioning the external support member in a predetermined relationship with an x-ray source and viewer, said x-ray alignment means comprising at least one radiodense tube secured to the rigid elongate external support member, a first radiodense plate in said tube and substantially aligned with the axis of said tube, and a second radiodense plate in said tube and substantially aligned with the axis of said tube, the plane of the second plate being substantially perpendicular to the plane of the first plate, the x-ray alignment means being so constructed and arranged as to appear as a circle having a symmetrical cross therein on an x-ray film when the x-ray source is aligned therewith.

The present invention greatly reduces the difficulty in locating fastening apertures and drilling holes in alignment therewith to accept the fastener screws. All but the final fine adjustments are made before the intramedullary rod is inserted, leaving only very small adjustments after insertion. The time to complete the surgery is greatly reduced and, as a result, the patient suffers less trauma from the surgery. The holes for inserting and receiving the fastener screws are drilled very precisely in alignment making it possible to provide very firm, stable fixation of the intramedullary rod in the femur.

Industrial Application

This invention finds application in human and veterinarian surgery.

What is claimed is:

1. An intramedullary rod targeting device for guiding drilling of distal fastener screw passages in the femur of a patient during the installation in the patient's femur of an intramedullary rod which comprises at least one fastener screw receiving aperture therethrough proximate the distal end thereof, comprising:

a rigid external support member adapted to reside outside the patient generally parallel to and along the patient's femur during installation of an intramedullary rod in the patient's femur, the external support member comprising an elongate channel support member comprising a web portion and edge flange portions, the web portion having formed therein connector screw apertures and alignment pin apertures;

means for removably mounting the proximal end of said intramedullary rod to and spaced from the proximal end of the external support member positioning the intramedullary rod generally parallel to the external support member with the axes of the fastener screw apertures in a predetermined relationship with respect to the rigid external support member, said means for mounting the proximal end of the intramedullary rod including an alignment pin for being received in an alignment pin aperture in the rigid external support member for accommodating specific intramedullary rods of specific lengths;

trochar alignment means movably mounted proximate the distal end of the external support member for being aligned with the axes of the fastener screw apertures through the intramedullary rod, the alignment pin and the corresponding alignment pin aperture being so positioned that for a specific intramedullary rod the trochar alignment means is aligned longitudinally with the fastener screw apertures; and means for adjusting the position and orientation of the trochar alignment means for guiding drills in the drilling of said fastener screw passages in the femur in alignment with the apertures through the distal end of the intramedullary rod.

2. The targeting device of claim 1 wherein the trochar alignment means comprising a an elongate trochar alignment block having first and second ends, a first trochar alignment tube passing through a first passage formed in the trochar alignment block proximate one end thereof and a second trochar alignment tube passing through a second passage formed in the trochar alignment block proximate the other end thereof, and means for adjusting the position and orientation of the trochar alignment means comprising a pivot on the trochar alignment block, a lateral screw drive threadably engaged with said pivot for moving the trochar alignment block laterally with respect to the intramedullary rod and screws mounted on the rigid elongate external support member for adjusting the angle of the trochar alignment block for aligning the trochar alignment tubes with the axes of the fastener passages in the intramedullary rod for adjusting the position and orientation of the trochar alignment means for guiding drills in the drilling of said fastener screw passages in the femur in alignment with the apertures through the distal end of the intramedullary rod.

3. The targeting device of claim 2 further comprising x-ray alignment means mounted on the external support member for positioning the external support member in a predetermined relationship with an x-ray source and viewer, said x-ray alignment means comprising at least one radiodense tube secured to the rigid elongate external support member, a first radiodense plate in said tube and substantially aligned with the axis of said tube, and a second radiodense plate in said tube and substantially aligned with the axis of said tube, the plane of the second plate being substantially perpendicular to the plane of the first plate, the x-ray alignment means being so constructed and arranged as to appear as a circle having a symmetrical cross therein on an x-ray film when the x-ray source is aligned therewith.

4. The targeting device of claim 1 further comprising x-ray alignment means mounted on the external support member for positioning the external support member in a predetermined relationship with an x-ray source and viewer, said x-ray alignment means comprising at least one radiodense tube secured to the rigid elongate external support member, a first radiodense plate in said tube and substantially aligned with the axis of said tube, and a second radiodense plate in said tube and substantially aligned with the axis of said tube, the plane of the second plate being substantially perpendicular to the plane of the first plate, the x-ray alignment means being so constructed and arranged as to appear as a circle having a symmetrical cross therein on an x-ray film when the x-ray source is aligned therewith.

5. An intramedullary rod targeting device for guiding drilling of distal fastener screw passages in the femur of a patient during the installation in the patient's femur of an intramedullary rod which comprises at least one fastener screw receiving aperture therethrough proximate the distal end thereof, comprising:
 a rigid elongate external support member adapted to reside outside the patient generally parallel to and along the patient's femur during installation of an intramedullary rod in the patient's femur;
 means for removably mounting the proximal end of said intramedullary rod to and spaced from the proximal end of the external support member positioning the intramedullary rod generally parallel to the external support member with the axes of the fastener screw apertures in a predetermined relationship with respect to the external support member;
 trochar alignment means movably mounted proximate the distal end of the external support member for being aligned with the axes of the fastener screw apertures through the intramedullary rod;
 means for adjusting the position and orientation of the trochar alignment means for guiding drills in the drilling of said fastener screw passages in the femur in alignment with the apertures through the distal end of the intramedullary rod; and
 x-ray alignment means mounted on the external support member for positioning the external support member in a predetermined relationship with an x-ray source and viewer, said x-ray alignment means comprising at least one radiodense tube secured to the rigid elongate external support member, a first radiodense plate in said tube and substantially aligned with the axis of said tube, and a second radiodense plate in said tube and substantially aligned with the axis of said tube, the plane of the second plate being substantially perpendicular to the plane of the first plate, the x-ray alignment means being so constructed and arranged as to appear as a circle having a symmetrical cross therein on an x-ray film when the x-ray source is aligned therewith.

6. An intramedullary rod targeting device for guiding drilling of distal fastener screw passages in the femur of a patient during the installation in the patient's femur of an intramedullary rod which comprises at least one fastener screw receiving aperture therethrough proximate the distal end thereof, comprising:
 a rigid elongate external support member adapted to reside outside the patient generally parallel to and along the patient's femur during installation of an intramedullary rod in the patient's femur;
 means for removably mounting the proximal end of said intramedullary rod to and spaced from the proximal end of the external support member positioning the intramedullary rod generally parallel to the external support member with the axes of the fastener screw apertures in a predetermined relationship with respect to the external support member;
 trochar alignment means movably mounted proximate the distal end of the external support member for being aligned with the axes of the fastener screw apertures through the intramedullary rod, the trochar alignment means comprising an elongate trochar alignment block having first and second ends, a first trochar alignment tube passing through a first passage formed in the trochar alignment block proximate one end thereof and a second trochar alignment tube passing through a second passage formed in the trochar alignment block proximate the other end thereof, and means for adjusting the position and orientation of the trochar alignment means comprising a pivot on the trochar alignment block, a lateral screw drive threadably engaged with said pivot for moving the trochar alignment block laterally with respect to the intramedullary rod and screws mounted on the rigid elongate external support member for adjusting the angle of the trochar alignment block for aligning the trochar alignment tubes with the axes of the fastener passages in the intramedullary rod for adjusting the position and orientation of the trochar alignment means for guiding drills in the drilling of said fastener screw passages in the femur in alignment with the apertures through the distal end of the intramedullary rod.

7. The targeting device of claim 6 further comprising x-ray alignment means mounted on the external support member for positioning the external support member in a predetermined relationship with an x-ray source and viewer, said x-ray alignment means comprising at least one radiodense tube secured to the rigid elongate external support member, a first radiodense plate in said tube and substantially aligned with the axis of said tube, and a second radiodense plate in said tube and substantially aligned with the axis of said tube, the plane of the second plate being substantially perpendicular to the plane of the first plate, the x-ray alignment means being so constructed and arranged as to appear as a circle having a symmetrical cross therein on an x-ray film when the x-ray source is aligned therewith.

* * * * *